(12) United States Patent
Hannula et al.

(10) Patent No.: US 7,190,986 B1
(45) Date of Patent: Mar. 13, 2007

(54) NON-ADHESIVE OXIMETER SENSOR FOR SENSITIVE SKIN

(75) Inventors: Don Hannula, San Luis Obispo, CA (US); Paul D. Mannheimer, Danville, CA (US)

(73) Assignee: Nellcor Puritan Bennett Inc., Pleasanton, CA (US)

( * ) Notice: Subject to any disclaimer, the term of this patent is extended or adjusted under 35 U.S.C. 154(b) by 0 days.

(21) Appl. No.: 10/274,845

(22) Filed: Oct. 18, 2002

(51) Int. Cl.
*A61B 5/00* (2006.01)

(52) U.S. Cl. .................. 600/344; 600/310; 600/323
(58) Field of Classification Search ........ 600/309–310, 600/322–323, 344
See application file for complete search history.

(56) References Cited

U.S. PATENT DOCUMENTS

| | | | | |
|---|---|---|---|---|
| 3,696,181 A | * | 10/1972 | Bonner, Jr. ................ | 264/53 |
| 4,830,014 A | | 5/1989 | Goodman et al. | |
| 4,953,552 A | * | 9/1990 | DeMarzo ................. | 600/347 |
| 5,246,003 A | * | 9/1993 | DeLonzor ................ | 600/344 |
| 5,478,824 A | * | 12/1995 | Burns et al. ............. | 351/172 |
| 5,584,296 A | * | 12/1996 | Cui et al. ................ | 600/479 |
| 5,758,644 A | * | 6/1998 | Diab et al. ............... | 600/323 |
| 5,797,841 A | * | 8/1998 | Delonzor et al. ......... | 600/323 |
| 5,830,136 A | * | 11/1998 | Delonzor et al. ......... | 600/323 |
| 5,913,819 A | * | 6/1999 | Taylor et al. ............. | 600/323 |
| 6,018,673 A | * | 1/2000 | Chin et al. ............... | 600/322 |
| 6,063,029 A | * | 5/2000 | Saita et al. .............. | 600/309 |
| 6,073,038 A | * | 6/2000 | Wang et al. .............. | 600/323 |
| 6,321,100 B1 | * | 11/2001 | Parker .................... | 600/344 |
| 6,342,285 B1 | * | 1/2002 | Shepard et al. .......... | 428/88 |
| 6,354,989 B1 | * | 3/2002 | Nudeshima ............. | 600/3 |
| 6,479,015 B1 | * | 11/2002 | Long et al. .............. | 422/58 |
| 6,615,062 B2 | * | 9/2003 | Ryan et al. .............. | 600/310 |
| 6,671,532 B1 | * | 12/2003 | Fudge et al. ............ | 600/344 |
| 6,731,963 B2 | * | 5/2004 | Finarov et al. .......... | 600/335 |
| 2002/0038082 A1 | * | 3/2002 | Chin ...................... | 600/323 |

OTHER PUBLICATIONS 3M product information for 1/32 inch PVC Foam Tape 9777-L, from 3M online product catalog.*

* cited by examiner

*Primary Examiner*—Eric F. Winakur
(74) *Attorney, Agent, or Firm*—Fletcher Yoder PC

(57) ABSTRACT

The present invention provides non-adhesive oximeter sensors for patients with sensitive skin. Sensors of the present invention include a light emitting diode (LED) and a photodetector. The LED and the photodetector may be covered by a reflective mask and a faraday shield. Sensors of the present invention have a non-adhesive laminated layer. The non-adhesive layer contacts, but does not stick to, the patient's skin. When the sensor is removed from the patient, the non-adhesive layer does not tear or irritate the patient's skin. The non-adhesive layer preferably has a large static coefficient of friction. Sensors of the present invention can also have hook-and-loop layers. The sensor can be attached to the patient's body by wrapping the sensor around the patient and engaging the hook layer to the loop layer.

71 Claims, 2 Drawing Sheets

NON-ADHESIVE OXIMETER SENSOR FOR SENSITIVE SKIN

BACKGROUND OF THE INVENTION

The present application relates to non-adhesive oximeter sensors, and more particularly to non-adhesive oximeter sensors for patients with sensitive skin.

Non-invasive monitoring of a patient's pulse is common in medical practice. One type of pulse oximeter monitor incorporates one or more light-emitting-diodes (LEDs) to shine through an area of tissue containing large amounts of blood. The light source is mounted to well-perfused tissue, such as a fingertip. Light is emitted and shines through the tissue. The amount of light passing through the tissue is measured using a photodetector.

Changes between the light emitted by the light source and the light received by the photodetector are caused by changes in the optical absorption of the light by the blood perfusing through the monitored tissue. The LEDs can emit either broad-spectrum visual light or narrow bandwidth light in the red or infrared wavelengths.

The absorption of certain wavelengths is related to the oxygen saturation level of hemoglobin in the blood perfusing the tissue. The variations in light absorption caused by change in oxygen saturations make possible direct measurement of the arterial oxygen content.

One type of prior art oximeter sensor is the STAT-WRAP™ sensor E542 by Epic Medical Equipment Services of Plano, Tex. The STAT-WRAP™ sensor has a non-adhesive foam outer layer that contacts a patient's skin. The foam layer is a thick, bulky layer relative to the overall thickness of the sensor. The foam layer has a static coefficient of friction of about 1.43.

The STAT-WRAP™ sensor also has hook-and-loop layers that engage each other. The hook layer is a separate layer that is stitched to an end of the sensor.

Other prior art oximeter sensors have an outer adhesive layer. The adhesive layer is a sticky material that bonds temporarily to the skin like a band-aid. The adhesive holds the oximeter sensor on the skin of the patient so that it does not move or fall off, while measurements are being taken.

Some patients (e.g., neonates) have sensitive skin that may tear or become irritated when adhesive material is applied to the skin and later removed. It would therefore be desirable to provide an oximeter sensor that remains attached to a patient's skin without using adhesive material, while avoiding the bulk of prior-art non-adhesive sensors. It would further be desirable to accomplish these two features in a manner that the sensor can be sterilized and produced economically.

BRIEF SUMMARY OF THE INVENTION

The present invention provides non-adhesive oximeter sensors for patients with sensitive or fragile skin. Sensors of the present invention include a light emitting diode (LED) and a photodetector. The LED light shines light through a patient's tissue. The light from the LED is detected by the photodetector. The LED and photodetector may be covered by transparent windows. The LED and the photodetector may also be covered by a reflective mask and a Faraday electromagnetic shield.

Sensors of the present invention have a laminated non-adhesive layer. The non-adhesive layer contacts, but does not stick to, the patient's skin. When the sensor is removed from the patient, the non-adhesive layer does not tear or irritate the patient's skin. Therefore, the non-adhesive layer protects sensitive skin. In one embodiment, the non-adhesive layer is a polyvinyl chloride foam material. The non-adhesive layer preferably has a large static coefficient of friction to help keep the sensor motionless relative to the patient.

Sensors of the present invention also include one or more laminated layers that hold the sensor unit on the patient's body. These layers may include hook and loop layers. The sensor can be attached to the patient's body by wrapping the sensor around the patient and engaging the hook layer to the loop layer.

Sensors of the present invention may include a strengthening layer that lies between the other laminated layers. Furthermore, sensors of the present invention may include light-blocking features to minimize or eliminate ambient light interference and LED light from reaching the photodetector without passing through blood-perfused tissues (shunting).

DETAILED DESCRIPTION OF THE INVENTION

Figure 1A:
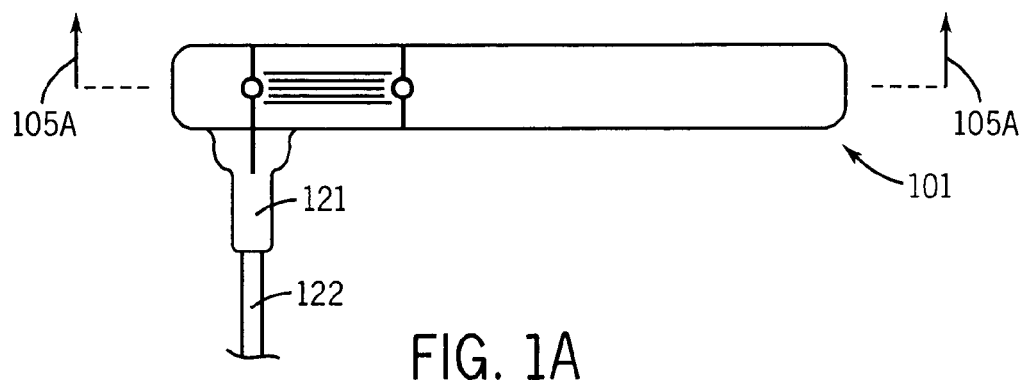
FIG. 1A illustrates a plan view of an exemplary embodiment of a non-adhesive oximeter sensor in accordance with the present invention.
Figure 1B:
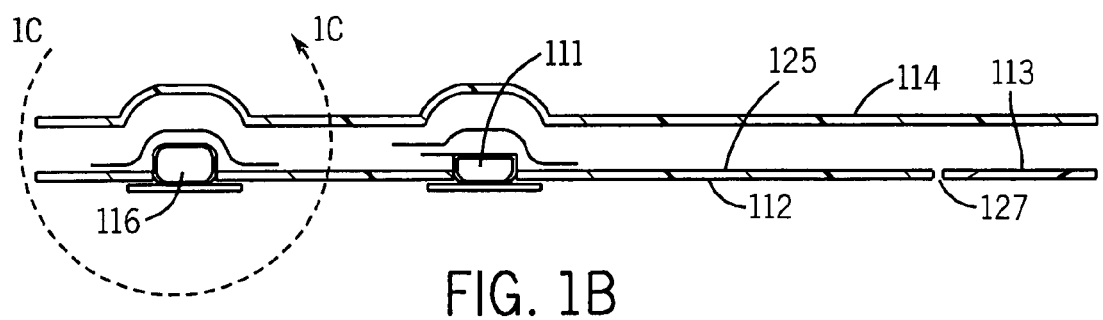
FIG. 1B illustrates a cross-sectional view of the sensor of FIG. 1A taken along line 105A—105A.
Figure 1C:
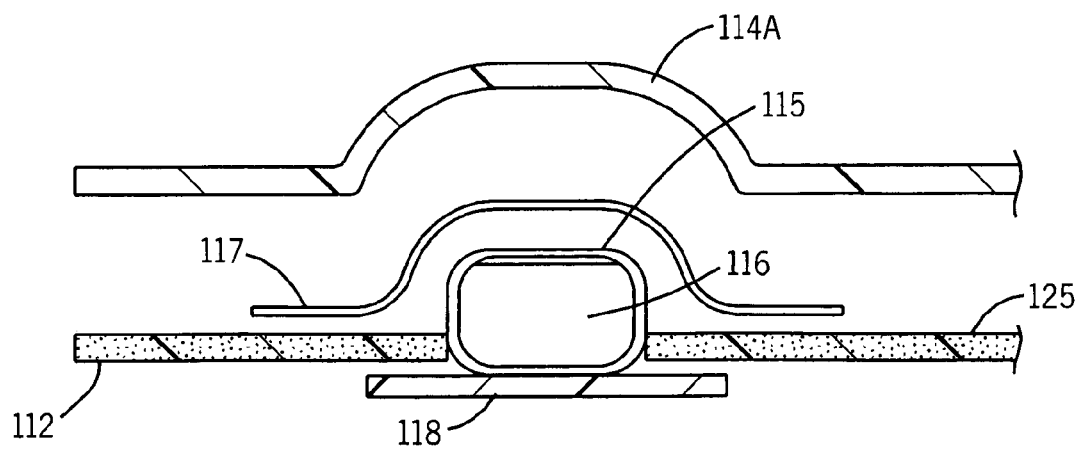
FIG. 1C illustrates a detailed view of a portion of FIG. 1B designated by the circle 1C.

Oximeter sensor 101 shown in FIGS. 1A, B, and C is an embodiment of the present invention. A top down view of oximeter sensor 101 is shown in FIG. 1A. A cross sectional view of oximeter sensor 101 along a plane 105A is shown in FIG. 1B. The cross sectional view shows the laminated layers of sensor 101. FIG. 1C illustrates an expanded view of a portion of the cross sectional view.

Oximeter sensor 101 has one or more light emitting diodes (LED) 111 and a photodetector 116 as shown in FIG. 1. LED 111 emits light that shines through a patient's tissue. The light from LED 111 is sensed by photodetector 116. Photodetector 116 produces a signal in response to the detected light. The signal is decoded by an oximeter monitor (not shown) to calculate the patient's blood oxygen saturation. LED 111 and photodetector 116 are connected to the oximeter monitor through wires that feed through cable 122.

Sensor 101 has a polyurethane window 118 below photodetector 116. Sensor 101 also has a polyurethane window below LED 111. The polyurethane windows are transparent. Light from LED 111 can pass unobstructed through the polyurethane windows to photodetector 116.

As shown in exploded view in FIG. 1C, photodetector 116, is surrounded by a reflective mask 117. Reflective mask 117 reflects light from LED 111 (that has passed through patient tissue and exited near the photodetector) back toward photodetector 116 like a mirror.

Reflective mask 117 increases the amount of LED light that the photodetector 116 receives from the patient's tissue, while assisting in blocking ambient light and LED light that may shunt through the laminated layers. LED 111 is also surrounded by a reflective mask that reflects light from LED 111 toward the patient's tissue. The reflective masks may comprise polyester or polypropylene with a reflective metal surface.

Photodetector 116 is also covered with a Faraday shield 115. Faraday shield 115 protects photodetector 116 from electromagnetic fields in the environment. Shield 115 reduces electromagnetic interference that may introduce noise into the output signal of photodetector 116.

Sensor 101 has laminated layers including layer 112 and hook-and-loop layers 113 and 114 shown in FIG. 1. Loop layer 114 has, for example, small loops of threads. Hook layer 113 has, for example, small hooks that engage with the loops in loop layer 114.

Hook layer 113 and loop layer 114 are used to attach sensor 101 to a patient. Hooks in hook layer 113 engage with the loops in loop layer 114. Once engaged, the hook-and-loop layers remain attached to each other, until they are pulled apart. The end user can engage and disengage hook layer 113 from loop layer 114 multiple times in order to open or close the fastener. One portion of layer 114 cannot attach to another portion of layer 114.

In one embodiment of the present invention, hook and loop layers 113 and 114 are VELCRO layers. In this embodiment, layer 114 comprises a VELCRO loop, and layer 113 comprises a VELCRO hook.

Loop layer 114 has a first raised portion 114A that provides room for the thickness of photodetector 116. Loop 114 also has a second raised portion that provides room for LED 111.

Sensor 101 also has a bottom laminated layer 112 as shown in FIG. 1. Layer 112 is a non-adhesive layer. Layer 112 is preferably made of a material that has a soft, smooth, non-skid surface. Layer 112 may, for example, comprise polyvinyl chloride (PVC) foam. One type of PVC that may be used with the present invention is 3M-9777L PVC foam manufactured by 3M Co. Layer 112 may also comprise other types of soft, non-adhesive material.

Bottom layer 112 is an outer layer of the sensor that contacts the patient's skin. Layer 112 comprises a non-adhesive material that does not adhere or stick to the patient's skin. Because layer 112 comprises a soft, non-adhesive material, it does not tear or irritate sensitive or fragile skin when sensor 101 is removed from the patient.

Layer 112 preferably comprises a material that has a relatively large static coefficient of friction. A material with a large static coefficient of friction helps to keep sensor 101 motionless relative to the skin as a patient moves. In sensors of the present invention, it is important to maximize the friction between the sensor and the skin, without the use of adhesives. Adhesives can damage fragile skin, and one objective of the present invention is to keep the sensor on the patient without slippage, but without the use of an adhesive.

According to the present invention, the static coefficient of friction of a material is tested using the following procedure. Attach a protractor to a vertical wall with the center in line with the edge of a table. Set up a stop block at the edge of the table to act as a pivot point for a glass plate. Place the glass plate flat on the table with one edge along the edge of the table, up against the stop block. Place a test sample of the material on the glass plate (or other reference materials, such as skin). Lift the free edge of the glass plate until the test sample just starts to slip. Record angle at which slippage first occurred. This angle is the angle of repose. Then calculate the coefficient of friction, which is the tangent of the angle of repose.

The coefficient of friction of polyvinyl chloride (PVC) foam is greater than the prior art foam wrap assembly found in the STAT-WRAP™ sensor. The 3M-9777L PVC foam measured using the above-described measuring technique resulted in a value of static coefficient of friction of infinity with respect to glass. The 3M-9777L PVC foam actually stayed on the glass test plate even after achieving a 90 degree angle of repose.

The 3M-9777L PVC material almost exhibits slight adhesive properties, surface tension forces, or static cling forces. Therefore, PVC foam is a very good choice of material for layer 112 in consideration of the preferred non-slip characteristics. Using skin as a reference material instead of glass, the 3M-9777L PVC foam exhibits a static coefficient of friction of greater than 5, such as 5.7.

The PVC material almost exhibits slight adhesive properties, surface tension forces, or static cling forces. Therefore, PVC foam is a very good choice of material for layer 112 in consideration of the preferred non-slip characteristics.

Materials other than PVC foam can be used for layer 112. The static coefficient of friction for layer 112 is preferably greater than 10. Most preferably, layer 112 has a static coefficient of friction that is greater than 100.

Layer 112 is preferably light in color to enhance the amplitude of the light signals received by photodetector 116. For example, layer 112 may be white, off-white, or cream colored. Alternatively, layer 112 may be dark in color to decrease the amount of ambient and shunted light that reaches the photodetector, at an expense of the amount of detected LED light signals.

Figure 2:
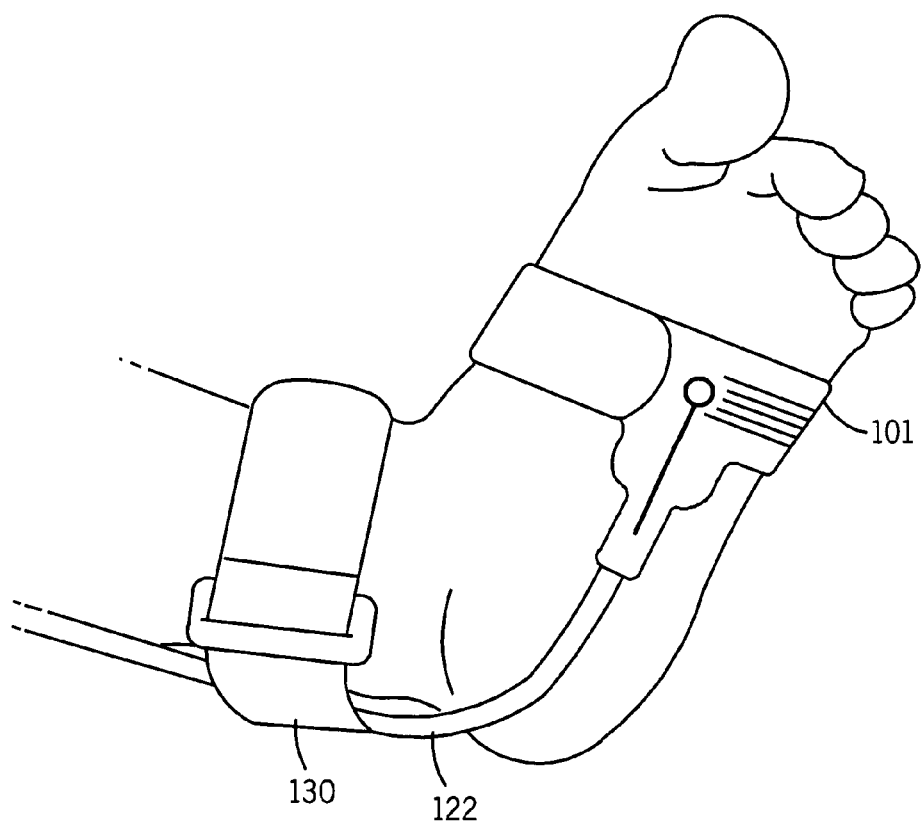
FIG. 2 illustrates how an embodiment of the non-adhesive oximeter sensor of the present invention can be placed on a patient's foot.

Layer 112 is preferably a thin layer, as shown in the cross sectional views in FIG. 1. By selecting a narrow thickness for layer 112, sensor 101 is less bulky. Because sensor 101 is thin, it is more flexible, and it can be easily conformed around a patient's body part. FIG. 2 illustrates an example of how sensor 101 can be placed around a patient's foot.

Sensor 101 may include an additional laminated layer. The additional laminated layer is a strengthening film (not shown) that lies between laminated layers 114 and 112. In one embodiment, hook layer 113 is attached to the strengthening film. In this embodiment, hook 113 is an integral part of one of the laminated layers that makes up the body of sensor 101. Hook portion 113 is not attached to layer 112. The foam layer 112 is discontinued at point 127 in FIG. 1, and hook portion 113 begins to the right of 127. In other embodiments, hook layer 113 is an integral part of bottom layer 112 or top layer 114.

In one embodiment of the present invention, the inner side 125 of layer 112 is covered with a laminated opaque film. The opaque film blocks ambient light that may interfere with photodetector 116. The opaque film may comprise polyethylene. The opaque film may be black or some other dark color that helps block ambient light and reduces shunted light. Dark in color is understood here to be of a nature with little reflectance of the wavelengths of light sensed by the sensor's photodetector.

Non-adhesive layer 112 is preferably long enough to wrap all the way around the patient's finger, toe, ear, or other portion of the body. Non-adhesive layer 112 is the only portion of sensor 101 that directly contacts the patient's skin. This feature of the present invention eliminates damage to the patient's skin that can be caused by adhesive portions of a sensor.

Once sensor 101 has been wrapped snuggly around the patient's finger, toe, or other body part, hook 113 is engaged with loop layer 114. Layer 114 is facing outward relative to the patient and does not contact the skin. Hook 113 engages with any portion of loop layer 114. The connection between hook 113 and loop 114 keeps sensor 101 firmly attached to the patient so that it does not fall off or move.

The laminated layers of sensor 101 are preferably thin layers. Non-adhesive layer 112 is preferably a thin, non-bulky layer. Because sensor 101 comprises thin laminated layers, sensor 101 has a low profile and can function much like a second skin. The laminated layers of sensor 101, when combined, are preferably less than 0.1 inches thick, and more preferably less than 0.75 inches thick.

Sensor 101 is also easily conformable to the shape of a patient's body part, because the laminated layers that make up sensor 101 are thin and flexible. Sensor 101 may be a single patient use (disposable) sensor.

Sensor 101, by virtue of the choice of materials used in the preferred embodiment and the simplicity of the lamination style construction, can be sterilized using conventional Ethylene Oxide (EO) methods and can be produced economically.

Sensor 101 can also have a portion 121 around the end of cable 122. Portion 121 includes loop material that wraps all the way around the circumference of cable 122 as shown in FIG. 1. Loop portion 121 provides additional area that hook 113 can attach to.

Referring again to FIG. 2, a strap 130 is attached to cable 122. Strap 130 includes hook-and-loop layers that engage each other. Strap 130 can be wrapped around a portion of the patient's body (e.g., the patient's ankle as shown in FIG. 2) to further secure sensor 101 to the patient. Strap 130 may be movably attached to cable 122 so that strap 130 can slide up and down the cable. This feature allows strap 130 to be placed at a position along cable 122 where it can be conveniently attached to the patient.

While the present invention has been described herein with reference to particular embodiments thereof, a latitude of modification, various changes, and substitutions are intended in the present invention. In some instances, features of the invention can be employed without a corresponding use of other features, without departing from the scope of the invention as set forth. Therefore, many modifications may be made to adapt a particular configuration or method disclosed, without departing from the essential scope and spirit of the present invention. It is intended that the invention not be limited to the particular embodiment disclosed, but that the invention will include all embodiments and equivalents falling within the scope of the claims.

What is claimed is:

1. An oximeter sensor comprising:
    a light emitting element;
    a light detecting element;
    a substrate adapted to support the light emitting element and the light detecting element, the substrate comprising a non-adhesive patient-contacting surface, the patient contacting-surface having a static coefficient of friction greater than 5 with respect to a patient's skin.

2. The oximeter sensor of claim 1 wherein:
    the substrate includes first and second receptacles, the light emitting element residing in the first receptacle, and the light detecting element residing in the second receptacle; and comprising:
    a transparent polyurethane layer that covers the first receptacle and the second-receptacle.

3. The oximeter sensor of claim 1 comprising:
    a hook portion and a loop portion coupled to the substrate, the hook portion being releasably coupleable to the loop portion to facilitate attaching the sensor to a patient.

4. The oximeter sensor of claim 1 wherein the first substrate predominantly has a thickness of less than 0.1 inch.

5. The oximeter sensor of claim 1 wherein:
    the substrate comprises polyvinyl chloride foam.

6. The oximeter sensor of claim 1 further comprising:
    a cable attached to the sensor; and
    a strap movably attached to the cable, wherein the strap can be attached to the patient.

7. The oximeter sensor of claim 1 further comprising:
    reflective mask layers over one or both of the light emitting element and light detecting element.

8. The oximeter sensor of claim 1 further comprising:
    faraday shields over one or both of the light emitting and light detecting elements.

9. The oximeter sensor of claim 1 further comprising:
    an opaque film that covers the inner surface of the first laminated layer.

10. The oximeter sensor of claim 9 wherein:
    the opaque film is dark in color.

11. A method for forming an oximeter sensor, the method comprising:
    providing a substrate having a surface that contacts a patient, the substrate comprising a non-adhesive material that has a static coefficient of friction greater than 5 with respect to the patient's skin, the non-adhesive material retaining the oximeter sensor on the patient without the use of an adhesive that contacts skin of the patient, the substrate having first and second receptacles; and
    placing a light emitting element in the first receptacle;
    placing a light detecting element in the second receptacle.

12. The method of claim 11 further comprising:
    placing a first transparent polyurethane layer over the light emitting element; and
    placing a second transparent polyurethane layer over the light detecting element.

13. The method of claim 11 further comprising:
    placing a first reflective layer over the light emitting element; and
    placing a second reflective layer over the light detecting element.

14. The method of claim 11 further comprising:
    placing a hook layer and a loop layer on the substrate, wherein the loop layer is adapted to engage with the hook layer.

15. The method of claim 11 wherein the substrate comprises polyvinyl chloride foam.

16. The method of claim 11 wherein the light emitting and light detecting elements include faraday shields.

17. An oximeter sensor comprising:
    a light emitting element;
    a light detecting element;
    a substrate on which the light emitting element and the light detecting element are disposed, the substrate comprising a non-adhesive patient-contacting surface, the patient-contacting surface having a static coefficient of friction greater than 10 with respect to glass.

18. The oximeter sensor of claim 17 further comprising:
    a hook portion and a loop portion coupled to the substrate, the hook portion being releasably coupleable to the loop portion to facilitate attaching the sensor to a patient.

19. The oximeter sensor of claim 17 wherein the substrate predominantly has a thickness less than 0.1 inch.

20. The oximeter sensor of claim 17 wherein:
    the substrate comprises polyvinyl chloride foam.

21. The oximeter sensor of claim 17 wherein:
the patient contacting surface has a static coefficient of friction greater than 100 with respect to glass.

22. The oximeter sensor of claim 17 wherein the substrate comprises at least two layers laminated together.

23. The oximeter sensor of claim 17 wherein the substrate comprises at least three layers laminated together, wherein at least one of the at least three layers comprises a strengthening layer.

24. A method for forming an oximeter sensor, the method comprising:
providing a substrate having a surface that contacts a patient, the substrate comprising a non-adhesive material that has a static coefficient of friction greater than 10 with respect to glass, the non-adhesive material retaining the oximeter sensor on the patient without the use of an adhesive that contacts skin of the patient, the substrate having first and second receptacles; and
placing a light emitting element in the first receptacle;
placing a light detecting element in the second receptacle.

25. The method of claim 24 further comprising:
placing a first transparent polyurethane layer over the light emitting element; and
placing a second transparent polyurethane layer over the light detecting element.

26. The method of claim 24 further comprising:
placing a first reflective layer over the light emitting element; and
placing a second reflective layer over the light detecting element.

27. The method of claim 24 further comprising:
placing a hook layer and a loop layer on the substrate, wherein the loop layer is adapted to engage with the hook layer.

28. The method of claim 24 wherein the substrate comprises polyvinyl chloride foam.

29. The method of claim 24 wherein the non-adhesive material has a static coefficient of friction greater than 100 with respect to glass.

30. An oximeter sensor comprising:
a light emitting element:
a light detecting element;
a substrate being strap-like in shape and configured to encircle a portion of a patient, the substrate adapted to support the light emitting element and the light detecting element, the substrate comprising a non-adhesive polyvinyl chloride material having a patient-contacting surface, the substrate having a thickness of less than 0.1 inch and being adapted to attach to itself for securement to the patient,
wherein the substrate comprises at least two layers laminated together.

31. The oximeter sensor of claim 30 wherein the patient contacting surface has a static coefficient of friction greater than 5 with respect to a patient's skin.

32. The oximeter sensor of claim 30 wherein the patient contacting surface has a static coefficient of friction greater than 10 with respect to glass.

33. The oximeter sensor of claim 30 wherein the patient contacting surface has a static coefficient of friction greater than 100 with respect to glass.

34. The oximeter sensor of claim 30 wherein the substrate comprises at least three layers laminated together, wherein at least one of the at least three layers comprises a strengthening layer.

35. An oximeter sensor comprising:
a light emitting element;
a light detecting element;
a substrate having a strap-like configuration configured encircle a portion of a patient and to attach to itself, the substrate being adapted to support the light emitting element and the light detecting element, the substrate comprising a non-adhesive patient-contacting surface, the patient contacting-surface having a static coefficient of friction greater than 5 with respect to the patient's skin.

36. The oximeter sensor of claim 35 wherein:
the substrate includes first and second receptacles, the light emitting element residing in the first receptacle, and the light detecting element residing in the second receptacle; and comprising:
a transparent layer that covers the first receptacle and the second receptacle.

37. The oximeter sensor of claim 35 comprising:
a hook portion and a loop portion coupled to the substrate, the hook portion being releasably coupleable to the loop portion to facilitate attaching the sensor to a patient.

38. The oximeter sensor of claim 35 wherein the substrate predominantly has a thickness of less than 0.1 inch.

39. The oximeter sensor of claim 35 wherein the substrate comprises polyvinyl chloride foam.

40. The oximeter sensor of claim 35 comprising:
a cable attached to the sensor; and
a strap movably attached to the cable, wherein the strap is configured to be attachable to the patient.

41. The oximeter sensor of claim 35 comprising:
reflective mask layers over one or both of the light emitting element and light detecting element.

42. The oximeter sensor of claim 35 comprising:
faraday shields over one or both of the light emitting and light detecting elements.

43. The oximeter sensor of claim 35 comprising:
an opaque film that covers the inner surface of the first laminated layer.

44. The oximeter sensor of claim 43 wherein:
the opaque film is dark in color.

45. A method for forming an oximeter sensor, the method comprising:
providing a substrate having a predominant thickness of less than 0.1 inch and having a surface that contacts a patient, the substrate comprising a non-adhesive material that has a static coefficient of friction greater than 5 with respect to the patient's skin, the non-adhesive material retaining the oximeter sensor on the patient without the use of an adhesive that contacts skin of the patient, the substrate having first and second receptacles; and
placing a light emitting element in the first receptacle;
placing a light detecting element in the second receptacle.

46. The method of claim 45 comprising:
placing a first transparent layer over the light emitting element; and
placing a second transparent layer over the light detecting element.

47. The method of claim 45 comprising:
placing a first reflective layer over the light emitting element; and
placing a second reflective layer over the light detecting element.

48. The method of claim 45 comprising:
placing a hook layer and a loop layer on the substrate, wherein the loop layer is adapted to engage with the hook layer.

49. The method of claim 45 wherein the substrate comprises polyvinyl chloride foam.

50. The method of claim 45 wherein the light emitting and light detecting elements include faraday shields.

51. An oximeter sensor comprising:
a light emitting element;
a light detecting element;
a substrate on which the light emitting element and the light detecting element are disposed the substrate having a strap-like configuration configured encircle a portion of a patient and to attach to itself, the substrate comprising a non-adhesive patient-contacting surface, the patient-contacting surface having a static coefficient of friction greater than 10 with respect to glass.

52. The oximeter sensor of claim 51 comprising:
a hook layer and a loop layer coupled to the substrate, the hook layer being configured to engage the loop layer to facilitate attaching the strap-like substrate to itself.

53. The oximeter sensor of claim 51 wherein the substrate predominantly has a thickness less than 0.1 inch.

54. The oximeter sensor of claim 51 wherein the substrate comprises polyvinyl chloride foam.

55. The oximeter sensor of claim 51 wherein the patient contacting surface has a static coefficient of friction greater than 100 with respect to glass.

56. The oximeter sensor of claim 51 wherein the substrate comprises at least two layers laminated together.

57. The oximeter sensor of claim 51 wherein the substrate comprises at least three layers laminated together, wherein at least one of the at least three layers comprises a strengthening layer.

58. A method for forming an oximeter sensor, the method comprising:
providing a substrate having a predominant thickness of less than 0.1 inch and having a surface that contacts a patient, the substrate comprising a non-adhesive material that has a static coefficient of friction greater than 10 with respect to glass, the non-adhesive material retaining the oximeter sensor on the patient without the use of an adhesive that contacts skin of the patient, the substrate having first and second receptacles; and
placing a light emitting element in the first receptacle;
placing a light detecting element in the second receptacle.

59. The method of claim 58 comprising:
placing a first transparent layer over the light emitting element; and
placing a second transparent layer over the light detecting element.

60. The method of claim 58 comprising:
placing a first reflective layer over the light emitting element; and
placing a second reflective layer over the light detecting element.

61. The method of claim 58 comprising:
placing a hook layer and a loop layer on the substrate, wherein the loop layer is adapted to engage with the hook layer.

62. The method of claim 58 wherein the substrate comprises polyvinyl chloride foam.

63. The method of claim 58 wherein the non-adhesive material has a static coefficient of friction greater than 100 with respect to glass.

64. An oximeter sensor comprising:
a light emitting element;
a light detecting element;
a substrate having a coefficient of friction greater than 10 with respect to glass, the substrate being adapted to support the light emitting element and the light detecting element, the substrate comprising a non-adhesive material having a patient-contacting surface, the substrate having a thickness of less than 0.1 inch and being adapted to attach to itself for securement to the patient.

65. The oximeter sensor of claim 64 comprising:
a hook portion and a loop portion coupled to the substrate, the hook portion being releasably coupleable to the loop portion to facilitate attachment of the substrate to itself for securement to the patient.

66. The oximeter sensor of claim 64 wherein the substrate comprises at least two layers laminated together.

67. The oximeter sensor of claim 64 wherein the substrate comprises at least three layers laminated together, wherein at least one of the at least three layers comprises a strengthening layer.

68. An oximeter sensor comprising:
a light emitting element;
a light detecting element;
a substrate having a coefficient of friction greater than 5 with respect to a patient's skin, the substrate being adapted to support the light emitting element and the light detecting element, the substrate comprising a non-adhesive material having a patient-contacting surface, the substrate having a thickness of less than 0.1 inch and being adapted to attach to itself for securement to the patient.

69. The oximeter sensor of claim 68 comprising:
a hook portion and a loop portion coupled to the substrate, the hook portion being releasably coupleable to the loop portion to facilitate attachment of the substrate to itself for securement to the patient.

70. The oximeter sensor of claim 68 wherein the substrate comprises at least two layers laminated together.

71. The oximeter sensor of claim 68 wherein the substrate comprises at least three layers laminated together, wherein at least one of the at least three layers comprises a strengthening layer.

* * * * *